(12) United States Patent
Regimand et al.

(10) Patent No.: US 9,964,471 B2
(45) Date of Patent: May 8, 2018

(54) WHEEL-TRACKING DEVICES AND RELATED SYSTEMS AND METHODS

(71) Applicant: InstroTek, Inc., Raleigh, NC (US)

(72) Inventors: Ali Regimand, Raleigh, NC (US); Danilo Guerini, Bergamo (IT); Lawrence H. James, Raleigh, NC (US); Paola Maestroni, Bergamo (IT); Andrew Thomas LaCroix, Raleigh, NC (US)

(73) Assignees: INSTROTEK, INC., Raleigh, NC (US); MATEST S.P.A. UNIPERSONALE, Treviolo, Bergamo (IT)

( * ) Notice: Subject to any disclaimer, the term of this patent is extended or adjusted under 35 U.S.C. 154(b) by 457 days.

(21) Appl. No.: 14/686,095

(22) Filed: Apr. 14, 2015

(65) Prior Publication Data
US 2015/0292989 A1    Oct. 15, 2015

Related U.S. Application Data

(60) Provisional application No. 61/979,428, filed on Apr. 14, 2014.

(51) Int. Cl.
| | |
|---|---|
| *G01N 1/28* | (2006.01) |
| *G01N 33/42* | (2006.01) |
| *G01N 33/38* | (2006.01) |
| *G01N 19/02* | (2006.01) |
| *G01N 3/56* | (2006.01) |

(52) U.S. Cl.
CPC .............. *G01N 1/28* (2013.01); *G01N 33/38* (2013.01); *G01N 33/42* (2013.01); *G01N 3/56* (2013.01); *G01N 19/02* (2013.01)

(58) Field of Classification Search
CPC ........... G01N 33/42; G01N 33/38; G01N 3/56
USPC ........................ 73/7–8, 104–105, 146, 865.6
See application file for complete search history.

(56) References Cited

U.S. PATENT DOCUMENTS

| | | | |
|---|---|---|---|
| 5,659,140 A * | 8/1997 | Jakob | ....................... G01N 3/56 73/788 |
| 5,773,496 A | 6/1998 | Grubba | |
| 5,795,929 A | 8/1998 | Grubba | |

(Continued)

OTHER PUBLICATIONS

Aschebrener T. et al., "Comparison of the Hamburg Wheel-Tracking Device and the Environmental Conditioning System to Pavements of Known Stripping Performance", U.S. Department of Transportation Federal Highway Administration, Jan. 1994, 108 pages.

(Continued)

*Primary Examiner* — Peter Macchiarolo
*Assistant Examiner* — Anthony W Megna Fuentes
(74) *Attorney, Agent, or Firm* — Myers Bigel, P.A.

(57) ABSTRACT

A wheel-tracking test device includes a housing, one or more test chambers in the housing, one or more load arm assemblies, and a drive mechanism. Each test chamber is configured to receive and hold one or more asphalt test samples. Each load arm assembly includes a weighted loading arm and a wheel rotatably connected to the loading arm. The drive mechanism is configured to move the load arm assembly from a load position in which the wheel is on a test sample held in the test chamber and a rest position by retracting the loading arm such that the wheel is lifted off the test sample.

20 Claims, 14 Drawing Sheets

(56) References Cited

U.S. PATENT DOCUMENTS

| | | | |
|---|---|---|---|
| 5,969,261 A | 10/1999 | McAlister et al. | |
| 5,987,961 A | 11/1999 | Harris et al. | |
| 6,125,685 A | 10/2000 | Collier et al. | |
| 7,082,839 B2 * | 8/2006 | Pyle | G01N 3/56 73/808 |

OTHER PUBLICATIONS

Aschenbrener T., Evaluation of Hamburg Wheel-Tracking Device to Predict Moisture Damage in Hot-Mix Asphalt, Transportation Research Record 1492, (1995) pp. 193-201.

Eurekalert "Hand-portable device detects biological agents", American Society for Microbiology, Public Release: Mar. 11, 2003, Retrieved from the internet on Aug. 13, 2015 at URL http://www.eurekalert.org/pub_releases/2003-03/asfm-hdd030703.php.

Federal Highway Administration Research and Technology, Bituminous Mixtures Laboratory, Apr. 13, 2014, Retrieved from the Internet on Aug. 13, 2015 at URL http://www.fhwa.dot.gov/research/tfhrc/labs/materialscomplex/mixtures/.

Federal Highway Administration, Bituminous Mixtures Laboratory, Hamburg Wheel-Tracking Device, Feb. 10, 1997, pp. 266-271.

Gundry et al. "Amplicon Melting Analysis with Labeled Primers: A Closed-Tube Method for Differentiating Homozygotes and Heterozygotes", *Clinical Chemistry*, 49:3, pp. 396-406 (2003).

Izzo R. et al., "Evaluation Of The Use of The Hamburg Wheel-Tracking Device for Moisture Susceptibility of Hot Mix Asphalt", Texas Department of Transportation, Feb. 26, 1999, 25 pages.

Park T., Lovell C.W., "Using Pyrolized Carbon Black From Waste Tires in Asphalt Pavement", Purdue University, School of Engineering, Indiana Department of Transportation, Joint Highway Research Project, Feb. 20, 1996, 350 pages.

AASHTO Designation: T 324-11, "Hamburg Wheel-Track Testing of Compacted Hot Mix Asphalt", Nov. 2011, 10 pages.

* cited by examiner

WHEEL-TRACKING DEVICES AND RELATED SYSTEMS AND METHODS

RELATED APPLICATION

This application claims priority from U.S. Provisional Application No. 61/979,428, filed Apr. 14, 2014, the disclosure of which is hereby incorporated herein in its entirety.

BACKGROUND

The asphalt-concrete used as a major component of an asphalt pavement typically consists of a mixture of about 5% asphalt and 95% rock aggregate by weight. Rutting and stripping are two major distresses which occur in pavements constructed of hot mix asphalt (HMA) or warm mix asphalt (WMA) pavement. Rutting is the formation of depressions in the pavement in the direction of traffic flow under the influence of a moving wheel load. Stripping is the physical separation of asphalt cement from aggregate and asphalt coated aggregates from one another.

"Wheel-tracking" tests, in which a loaded wheel repeatedly travels across pavement or laboratory prepared samples or specimens to simulate the action of traffic, have been utilized to predict the rutting and/or stripping potential of the HMA pavement samples. One wheel-tracking test uses the Hamburg wheel-tracking device, developed by Helmut-Wind, Inc. of Hamburg, Germany. In the standard Hamburg test, two HMA specimens are submerged in water maintained at 50° C. (122° F.) and loaded by a wheel with a wheel load of 705 N (158 lbf). The test is performed to a maximum of 20,000 passes of the wheel over the specimen or until a specimen deformation of 20 mm (0.79 in) is recorded.

With known wheel-tracking devices, a heavy loading arm (i.e., one that imparts a wheel load of 705 N or 158 lbf on the specimen) is manually lifted by an operator or by a winch (which an operator must connect prior to the lifting). Also with known devices, an operator lifts a heavy tray with two cylindrical specimens or a slab specimen weighing between 35 and 50 pounds and typically seats the tray on brackets or the like in the water bath without any mechanical assistance.

SUMMARY

The present invention relates to improvements to an apparatus and method for evaluating asphalt samples. In another aspect, the present invention relates to a wheel tracking apparatus and method to evaluate the rutting and stripping potential of hot mix asphalt concrete samples. In still another aspect, the present invention relates to an improvement in a wheel tracking apparatus and method to insert, test, and remove asphalt samples.

There is a need for an improved apparatus and method in which the loading arm(s) are automatically moved to a "rest" position to allow for the insertion and removal of the testing trays. There is a further need for an improved apparatus and method that facilitates easier and safer insertion and removal of the testing trays when the loading arm is in the rest position.

Some embodiments of the present invention are directed to a wheel-tracking test device. The wheel-tracking test device includes a housing, one or more test chambers in the housing, one or more load arm assemblies, and a drive mechanism. Each test chamber is configured to receive and hold one or more asphalt test samples. Each load arm assembly includes a weighted loading arm and a wheel rotatably connected to the loading arm. The drive mechanism is configured to move the load arm assembly from a load position in which the wheel is on a test sample held in the test chamber and a rest position by retracting the loading arm such that the wheel is lifted off the test sample.

In some embodiments, when the load arm assembly is in the load position, the drive mechanism is configured to move the wheel to reciprocate over the one or more test samples.

In some embodiments, each test chamber includes a tray receiving unit that is configured to receive and hold a sample tray that holds the one or more test samples. The tray receiving unit may include one or more rails that slope downwardly from a front portion of the housing, with each rail configured to receive a front portion of a sample tray such that the sample tray can be slid down the one or more rails and into the test chamber. The tray receiving unit may include a tray holding member, with the tray holding member having a flat upper portion configured to hold the sample tray and the one or more test samples in a horizontal position. The tray receiving member may include one or more locking mechanisms configured to hold the sample tray in place in the horizontal position.

In some embodiments, the device is in combination with a sample tray holding one or more hot mix asphalt samples. The sample tray may include: a tray body; a sample holding member on a top surface of the tray body with the one or more samples held in the sample holding member; one sliding mechanism on each opposite side of the tray body at a front portion of the tray body; a first handle at the front portion of the tray body; and/or a second handle at a rear portion of the tray body.

In some embodiments, the device is a test device in compliance with AASHTO T324.

In some embodiments, the housing has a ramp engagement member, each load arm assembly has a ramp on a bottom portion of the loading arm, and the drive mechanism is configured to move the load arm assembly from the load position to the rest position by retracting the loading arm such that the ramp engages the ramp engagement member and the wheel is lifted off the test sample. In the rest position, a flat portion of the ramp may sit on the ramp engagement member.

In some embodiments, an actuator resides above the loading arm and vertically translates to pivot an end portion of the arm and raise/lower the wheel.

In some embodiments, the weighted loading arm includes at least one weight at a distal end portion of the arm. The weighted loading arm may have a weight that applies a wheel load of about 705 N or 158 lbf on the test sample in the load position.

In some embodiments, when the load arm assembly is in the load position, the drive mechanism is configured to move the wheel to reciprocate over the one or more test samples such that the position of the wheel varies sinusoidally over time.

Some other embodiments of the present invention are directed to a method of performing a asphalt sample test. The method includes: slidably inserting a sample tray holding one or more asphalt samples into a test chamber; automatically advancing a weighted load arm assembly to a load position using a drive mechanism, wherein in the load position a wheel of the load arm assembly is on the one or more asphalt samples; automatically reciprocating the wheel over the one or more samples using the drive mechanism to perform a wheel-track test; automatically retracting the load arm assembly to a rest position using the drive mechanism, wherein in the rest position the wheel is off the asphalt samples; and slidably removing the sample tray from the test chamber.

In some embodiments, the retracting step is carried out to retract and pivot the load arm assembly to raise the wheel off the one or more asphalt samples before the slidably removing step.

In some embodiments, the reciprocating step is carried out to perform a wheel-track test in compliance with AASHTO T324.

It is noted that any one or more aspects or features described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

DETAILED DESCRIPTION OF EMBODIMENTS OF THE INVENTION

Figure 1:
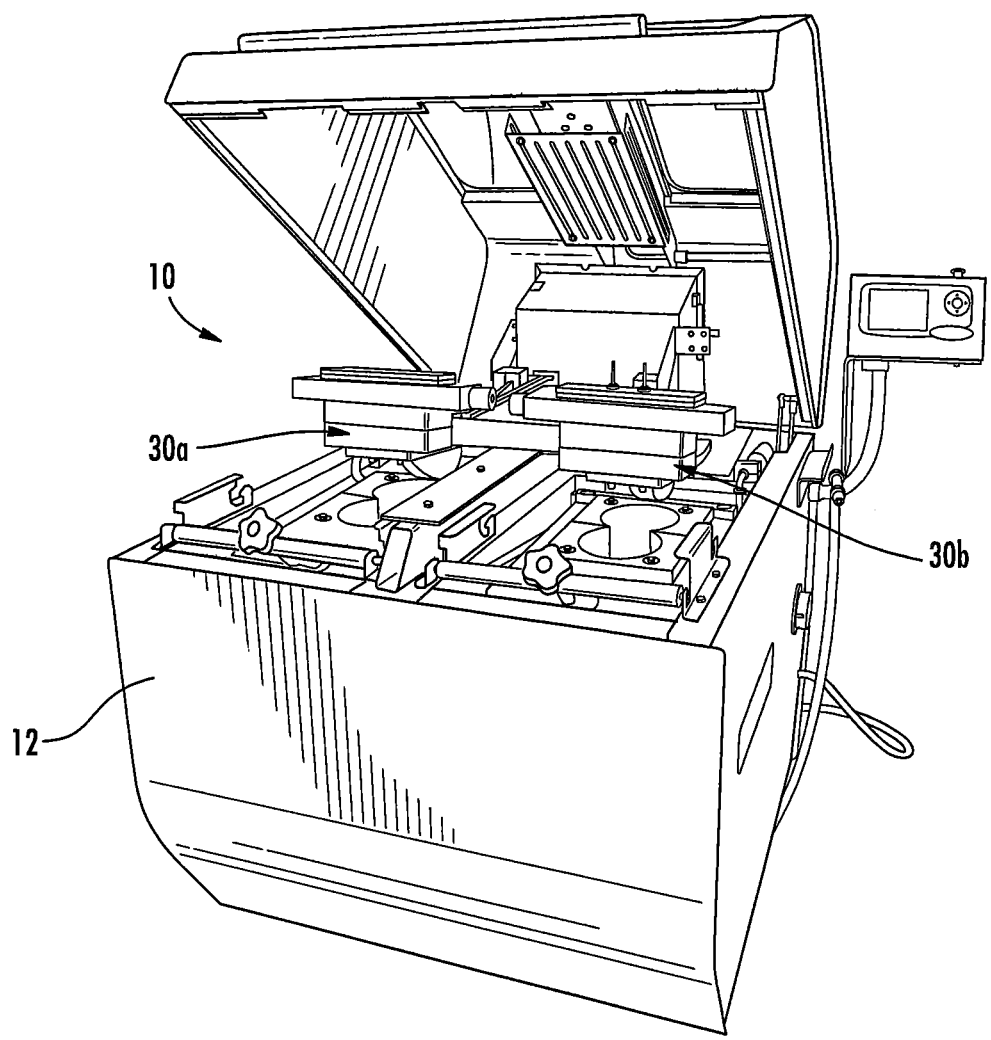
FIG. 1 is a perspective view of a wheel tracking device according to some embodiments.

The present invention now will be described more fully hereinafter with reference to the accompanying drawings, in which illustrative embodiments of the invention are shown. In the drawings, the relative sizes of regions or features may be exaggerated for clarity. This invention may, however, be embodied in many different forms and should not be construed as limited to the embodiments set forth herein; rather, these embodiments are provided so that this disclosure will be thorough and complete, and will fully convey the scope of the invention to those skilled in the art.

It will be understood that when an element is referred to as being "coupled" or "connected" to another element, it can be directly coupled or connected to the other element or intervening elements may also be present. In contrast, when an element is referred to as being "directly coupled" or "directly connected" to another element, there are no intervening elements present. Like numbers refer to like elements throughout.

In addition, spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein the expression "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The term "about" means the recited numerical value can vary by ±20%.

Figure 2:
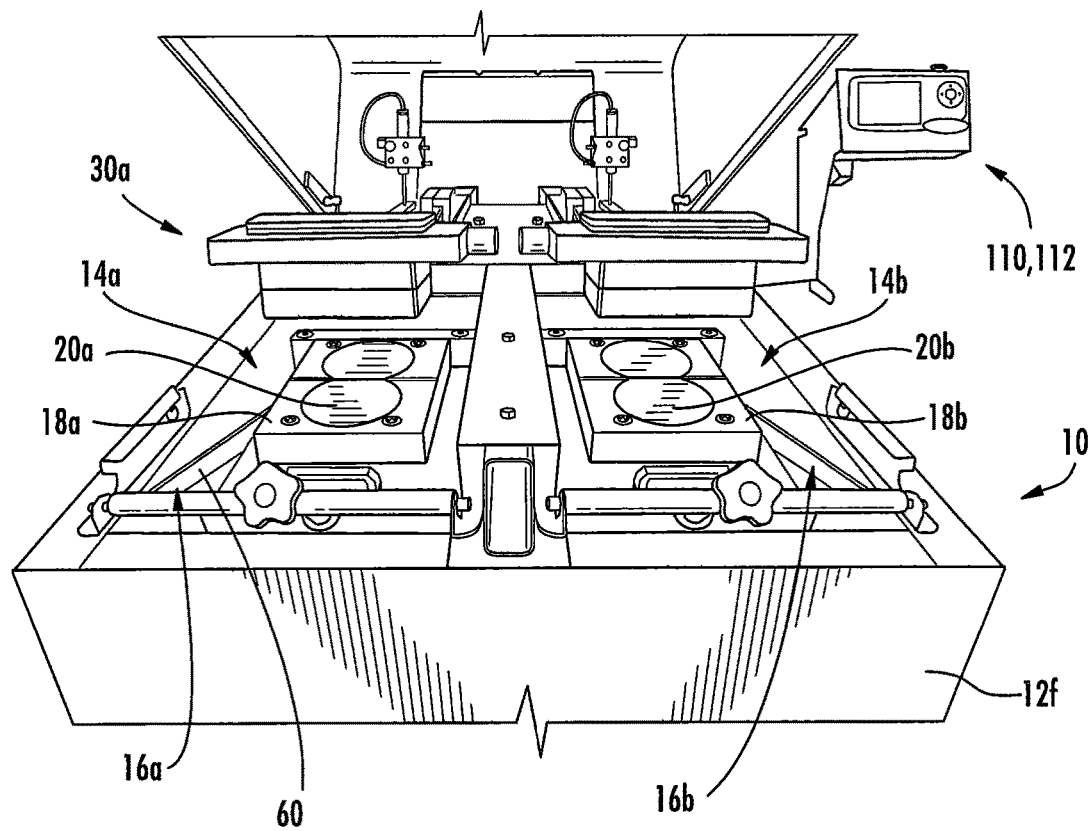
FIG. 2 is a fragmentary perspective view of the wheel tracking device of FIG. 1.

A wheel-tracking device 10 according to some embodiments is illustrated in FIGS. 1 and 2. The device 10 may be Hamburg wheel-tracking machine that meets the requirements of AASHTO T324, entitled "Hamburg Wheel-Track Testing of Compacted Hot Mix Asphalt (HMA)." AASHTO T324-11 (cited in an Information Disclosure Statement) is incorporated by reference in its entirety. The device 10 may meet any standard that is equivalent to and/or supersedes AASHTO T324.

As shown, the device 10 includes a frame or housing 12. First and second test chambers 14a, 14b are in the housing 12 (FIG. 2). A first tray holding unit 16a is in the first chamber 14a and is configured to receive and hold a first sample tray 18a. The first sample tray 18a is configured to hold one or more test samples or specimens 20a (e.g., HMA or WMA samples or specimens). A second tray holding unit 16b is in the second chamber 14b and is configured to receive and hold a second sample tray 18b. The second sample tray 18b is configured to hold one or more test samples or specimens 20b (e.g., HMA or WMA samples or specimens).

The device 10 also includes first and second load arm assemblies 30a, 30b. In the illustrated embodiment of FIGS. 1 and 2, the first and second test chambers 14a, 14b, the first and second tray holding units 16a, 16b and the first and second load arm assemblies 30a, 30b are substantially similar and can be the same. Accordingly, only the chamber 14a, the first tray loading unit 16a and the first load arm assembly 30a will be described in detail below. It is contemplated that the device 10 may include only one test chamber, only one tray holding unit, and only one load arm assembly (for example, the device 10 may include only the first test chamber 14a, the first tray holding unit 16a and the first load arm assembly 30a).

Figure 3:
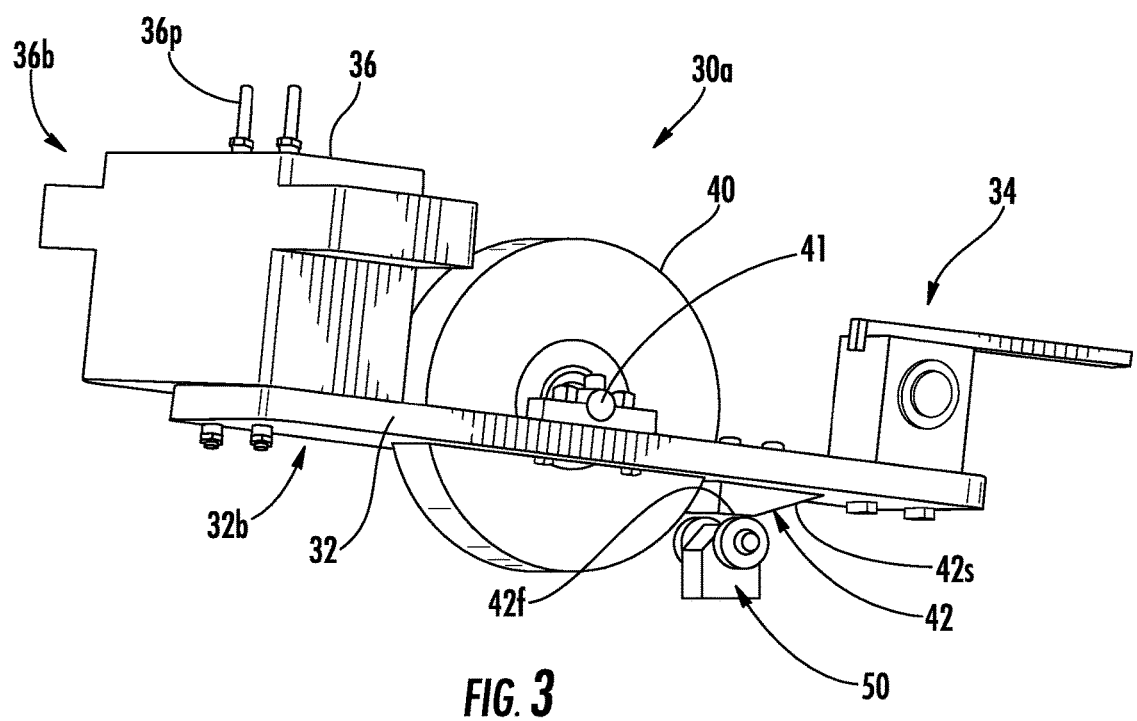
FIG. 3 is a perspective view of a load arm assembly according to some embodiments.

The load arm assembly 30a is shown in greater detail in FIGS. 3 and 4. As illustrated in FIG. 3, the load arm assembly 30a includes a loading arm 32 with a horizontal displacement member 34 at a proximal end portion of the arm 32 and a weight 36 at a distal end portion of the arm 32. There may be a weight bracket 36b that holds the weight 36. The weight bracket 36b may include upwardly extending projections 36p that are configured to receive additional weights as needed for a particular test (e.g., adjustable weight stacks). As used herein, the term "weighted load arm assembly" or "weighted load arm" means that the load arm assembly 30a includes the weight 36 and/or weight(s) stacked thereon such that the wheel 40 produces a substantial load on the samples (20a, 20b) (e.g., a wheel load of about 705 N or 158 lbf).

The load arm assembly 30a includes a wheel 40. The wheel 40 can extend through a channel in the arm 32. A shaft 41 rotatably couples the wheel 40 to the arm 32. The wheel 40 is rotatable about an axis defined by the shaft 41.

Figure 8:
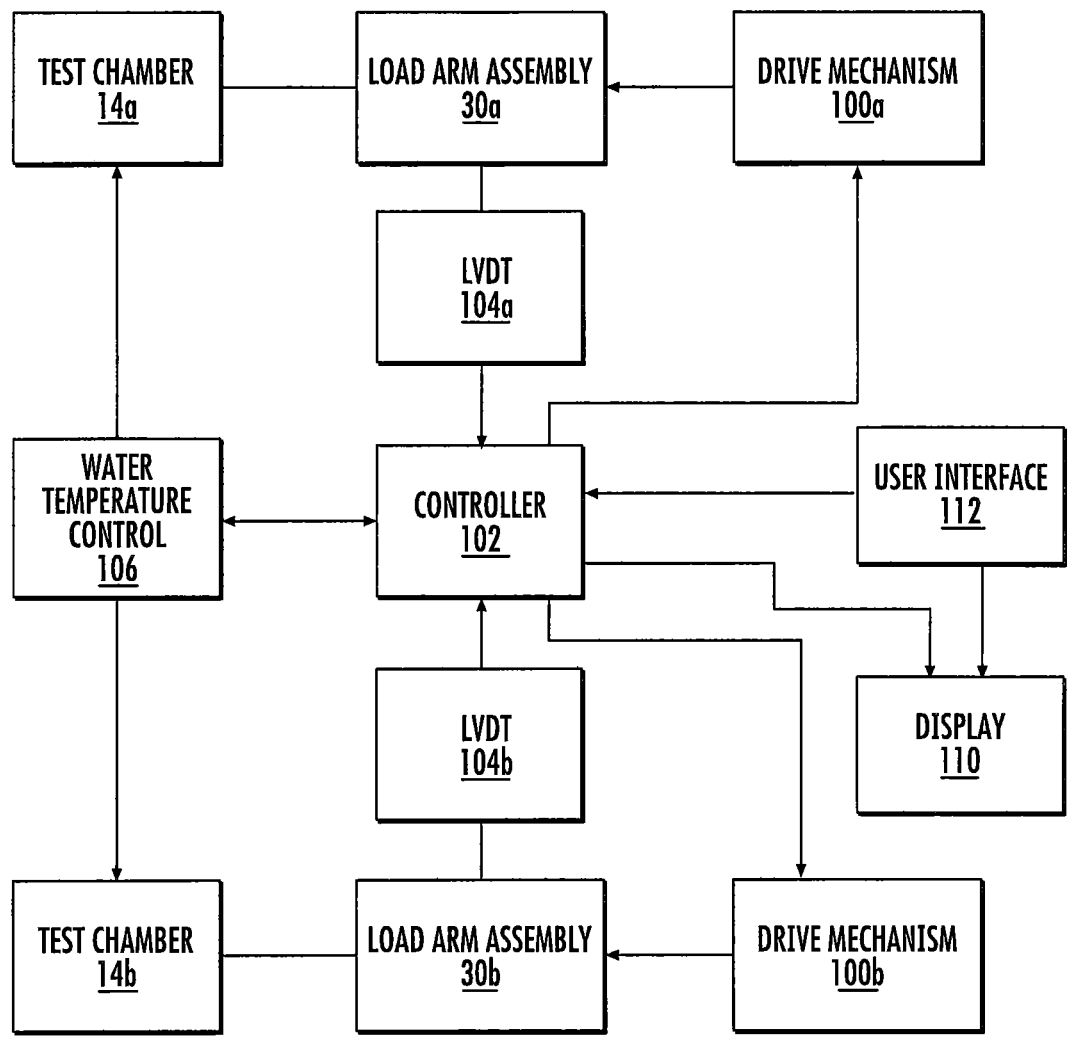
FIG. 8 is a block diagram illustrating features of the device of FIG. 1 according to some embodiments.

The load arm assembly 30a is movable in a horizontal or generally horizontal direction by a drive mechanism 100a (FIG. 8). The drive mechanism 100a may be operatively connected to the load arm assembly 30a (e.g., operatively connected to the horizontal displacement member 34) to drive the load arm assembly 30a in a horizontal or generally horizontal direction.

As illustrated in FIG. 3, the load arm assembly 30a includes a ramp or ramp member 42 extending under a bottom portion 32b of the arm 32. As illustrated, the ramp 42 includes a sloped portion 42s and a flat portion 42f. The ramp 42 is shown engaged with a ramp engagement member 50 in FIG. 3.

Figure 4A:
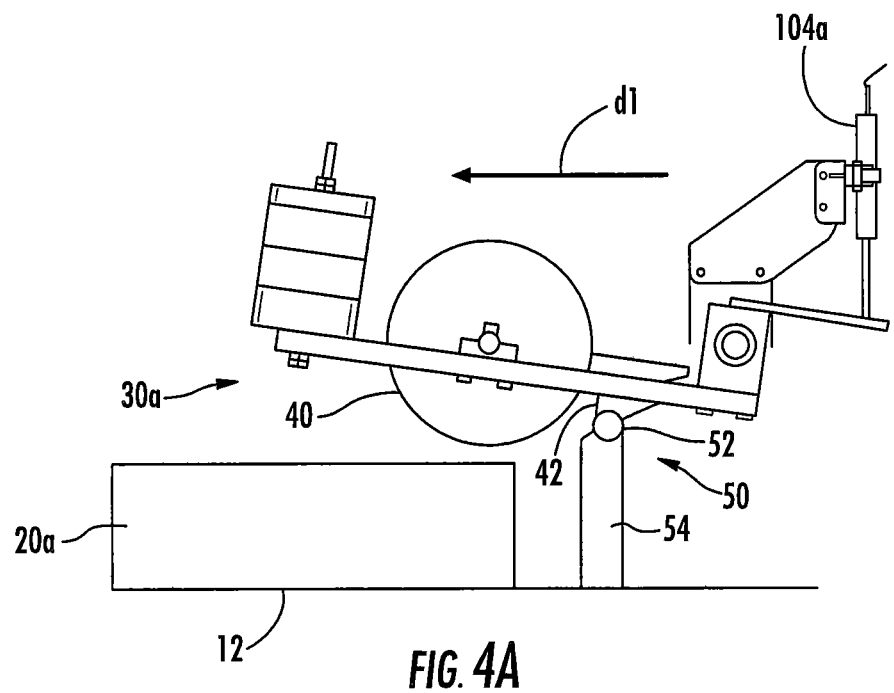
FIG. 4A is a side view of the load arm assembly of FIG. 3 in a rest position.
Figure 4B:
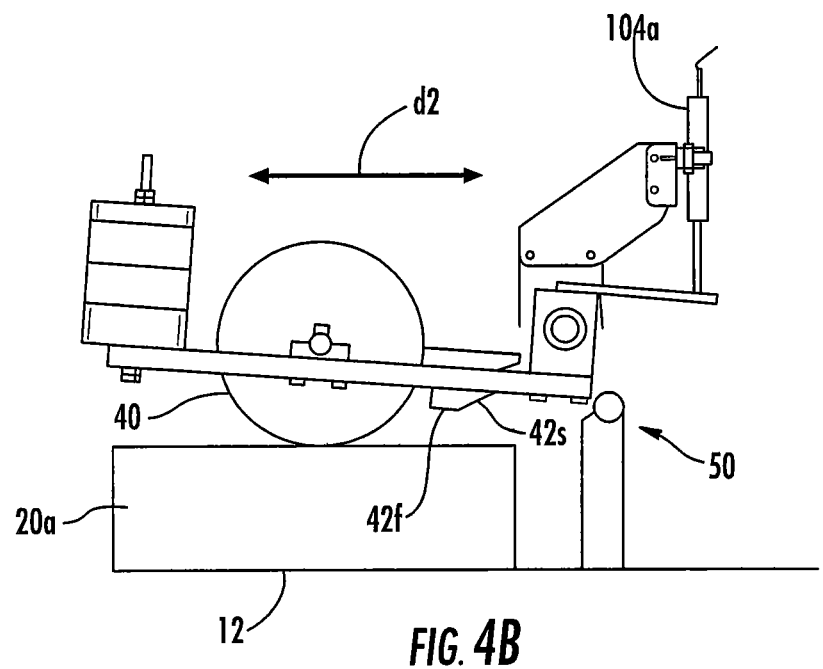
FIG. 4B is a side view of the load arm assembly of FIG. 3 in a load position.

Turning to FIGS. 4A and 4B, the drive mechanism 100a (FIG. 8) is configured to move the load arm assembly 30a (and hence the wheel 40) between a rest position and a load position. The load arm assembly 30a is shown in the rest position in FIG. 4A. In the rest position, the ramp 42 rests on the ramp engagement member 50 and the wheel 40 is raised off the sample 20a. The ramp engagement member 50 may include a roller 52 and a base 54, with the base 54 integrated with or attached to the device housing 12 (for example, the ramp engagement member may be in the test chamber 14a). The ramp flat portion 42f may rest or sit on the roller 52 in the rest position.

The drive mechanism 100a (FIG. 8) is configured to move the load arm assembly 30a in the direction shown by arrow d1 from the rest position to the load position. In the load position, as shown in FIG. 4B, the ramp 42 and the ramp engagement member 50 are no longer engaged and the wheel 40 is on the sample 20a. The drive mechanism 100a is configured to oscillate or reciprocate the wheel 40 back and forth over the sample 20a during a test as shown by the arrow d2. To move the load arm assembly 30a from the rest to load position an automated actuator can press down on the proximal end portion of the load arm 32. The actuator can comprise a transducer to vertically displace the load arm 32 between defined vertical positions.

This is further illustrated in FIGS. 5A-5D which are side views of the device 10 (partially deconstructed) in operation. A sample tray is not held in the tray holding unit 16a in the illustrated embodiment. Instead, the wheel 40 engages a flat tray supporting member 62 of the tray holding unit 16a in FIGS. 5A-5D. During a normal test, a sample tray holding one or more asphalt samples will be held in a horizontal position on and above the flat member 62 as described in more detail below. However, for ease of discussion, the flat member 62 will be referred to as the "asphalt sample" in the description of FIGS. 5A-5D below.

Figure 5A:
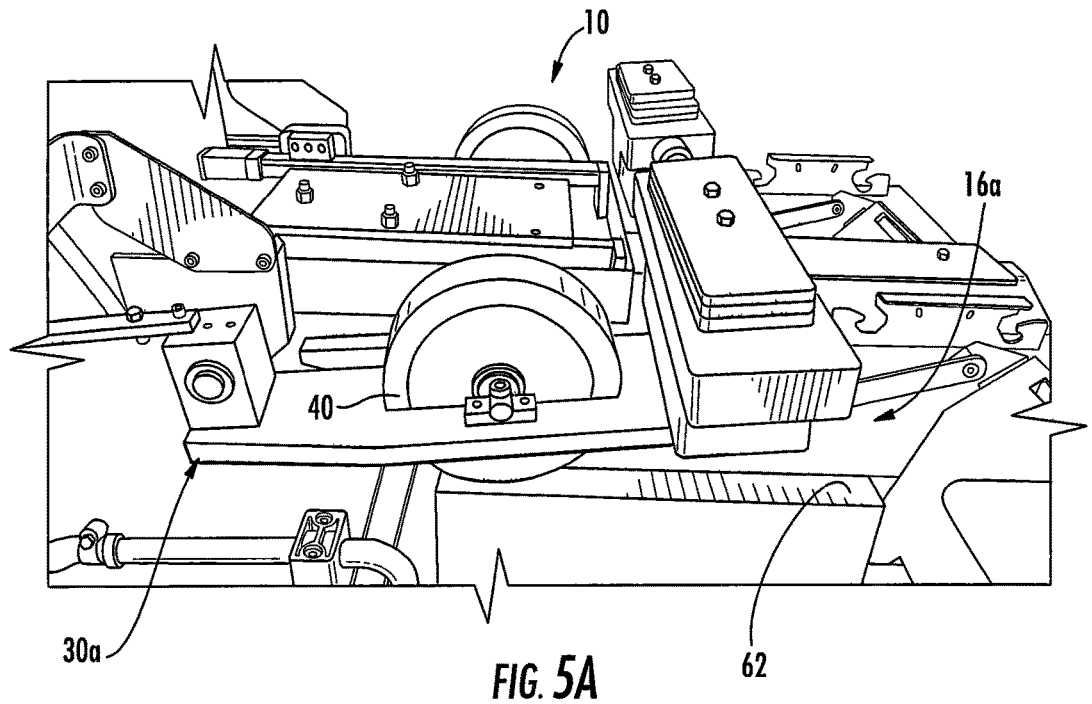
FIG. 5A is a fragmentary side view of the device of FIG. 1 (partially deconstructed) with a load arm assembly and a wheel in a rest position according to some embodiments.
Figure 5B:
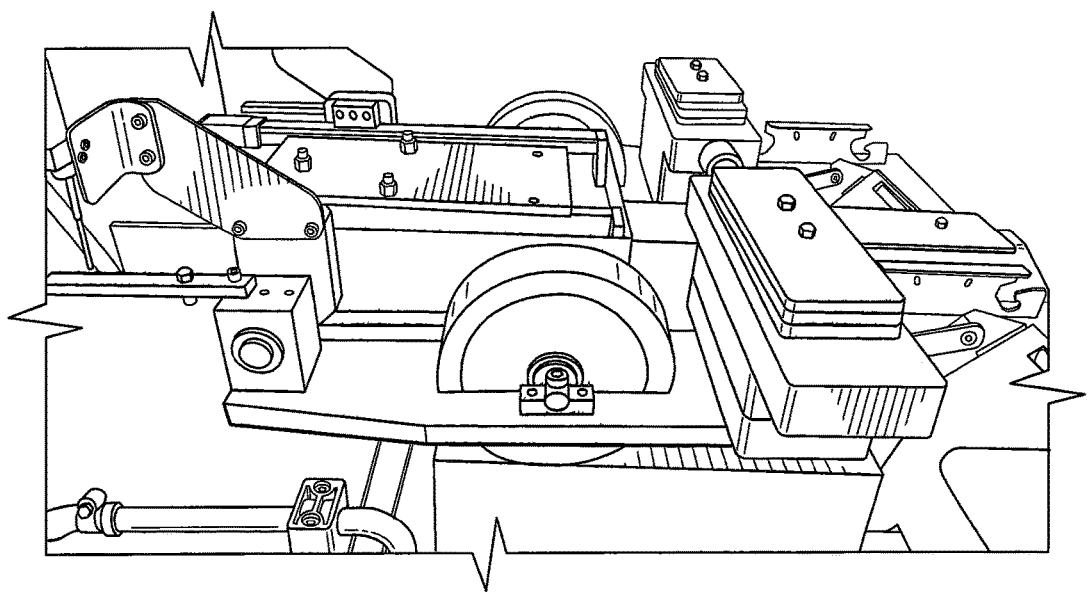
FIG. 5B illustrates the device of FIG. 5A with the load arm assembly and the wheel in a load position.
Figure 5C:
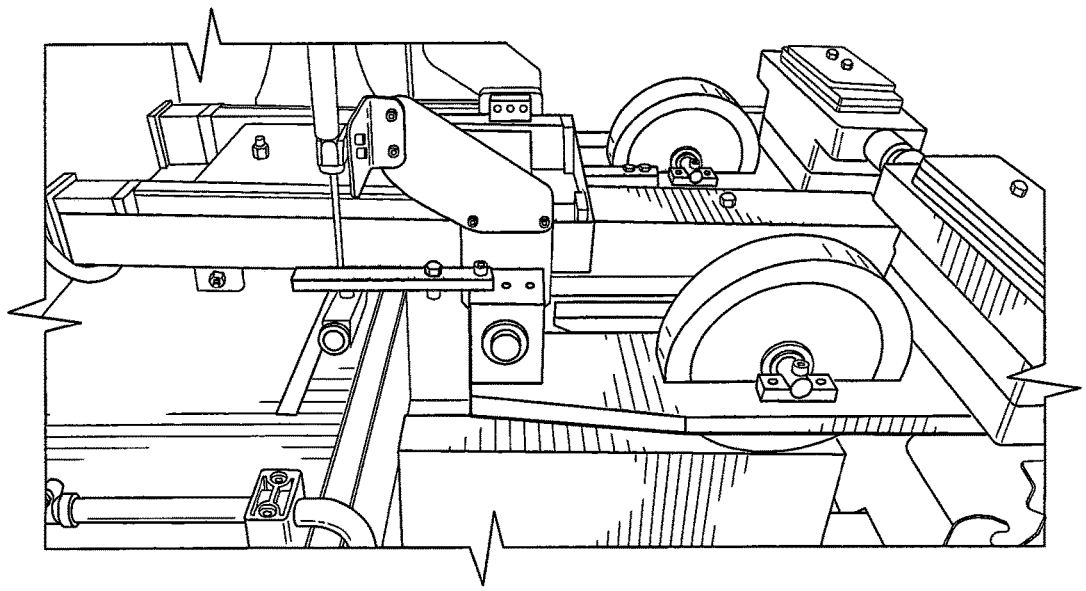
FIGS. 5C and 5D illustrate an operational sequence of the device of FIG. 5B with the wheel reciprocating over an asphalt sample.
Figure 5D:
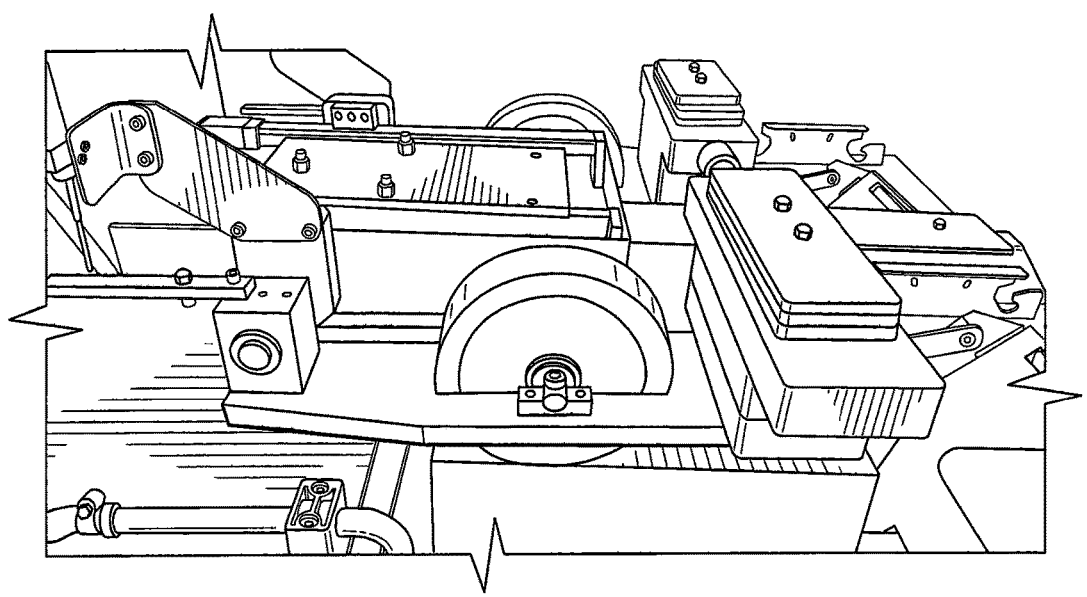
Figure 10:
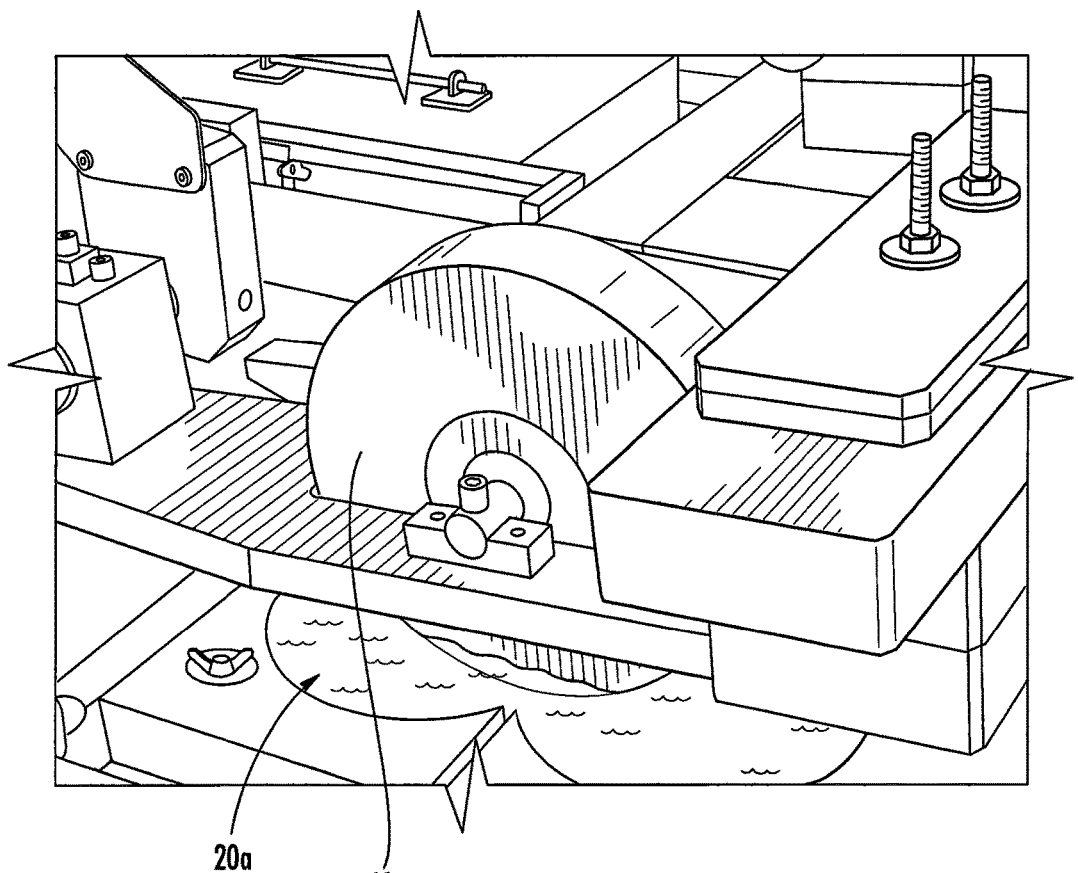
FIG. 10 is a fragmentary perspective view of the device of FIG. 1.

The load arm assembly 30a and the wheel 40 are shown in the rest position in FIG. 5A (this corresponds to the position shown in FIG. 4A). In the rest position, the wheel 40 is raised above the asphalt sample. The drive mechanism 100a (FIG. 8) is configured to advance the load arm assembly 30a with the wheel 40 to the load position which pivots the wheel 40 down as shown in FIG. 5B. In the load position, the wheel 40 is on the asphalt sample. As shown in FIGS. 5C and 5D, the drive mechanism 100a is configured to reciprocate the wheel 40 back and forth over the asphalt sample. See also FIG. 10, which shows the wheel 40 on the asphalt sample(s) 20a.

Figure 6A:
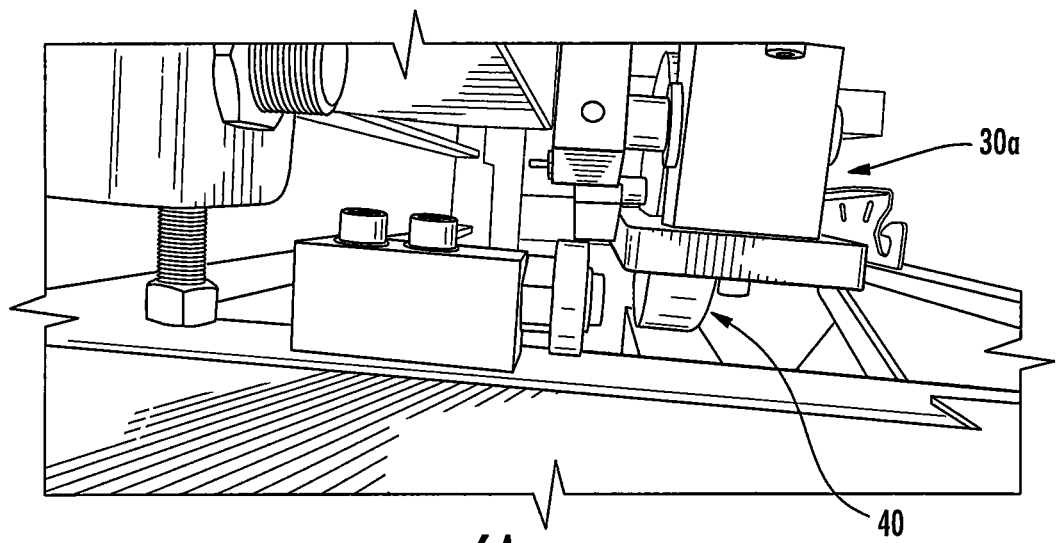
FIGS. 6A-6F illustrate an operational sequence of the device of FIG. 1 (partially deconstructed) with a load arm assembly and a wheel retracting to a rest position.
Figure 6B:
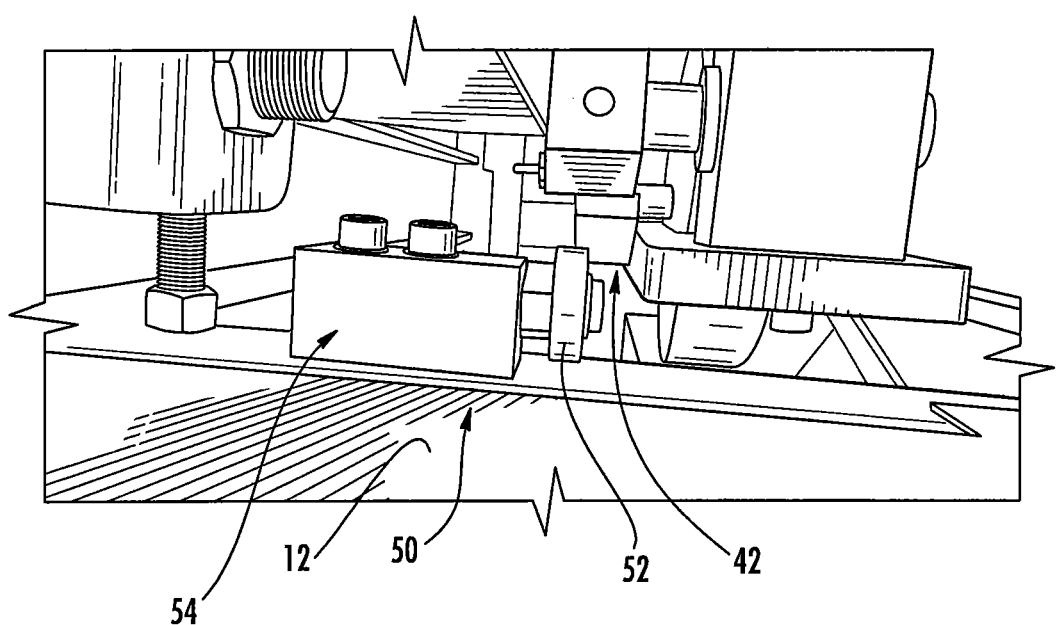
Figure 6C:
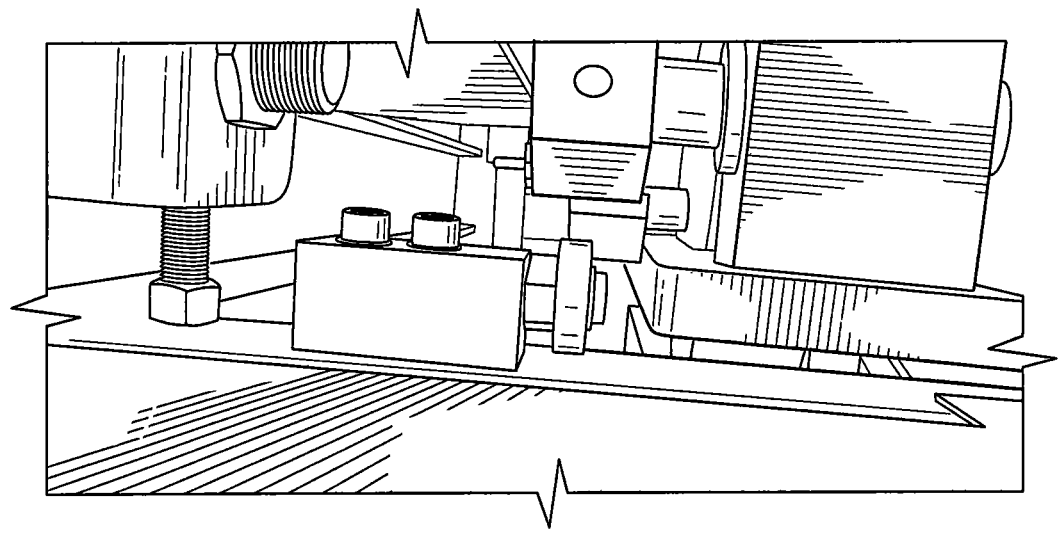

The drive mechanism 100a (FIG. 8) is also configured to retract the load arm assembly 30a and the wheel 40 to the rest position as illustrated in FIGS. 6A-6F. The drive mechanism 100a retracts the load arm assembly 30a such that the ramp 42 approaches the ramp engagement member 50 as shown in FIGS. 6A-6C. As shown in FIG. 6B, the base 54 of the ramp engagement member 50 may be mounted to the housing 12 and the roller 52 may be raised above the housing 12 and may be rotatable relative to the base 54.

Figure 6D:
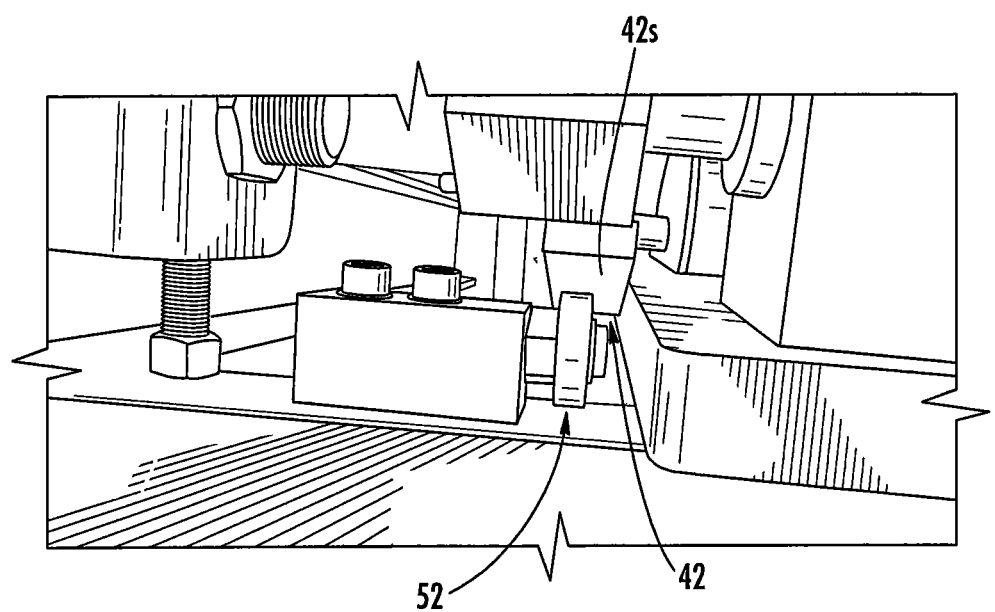
Figure 6E:
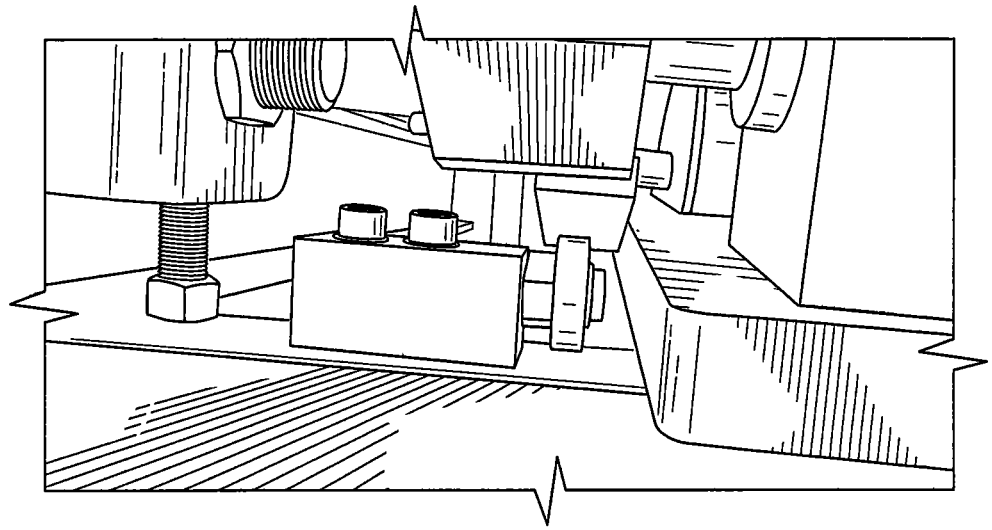
Figure 6F:
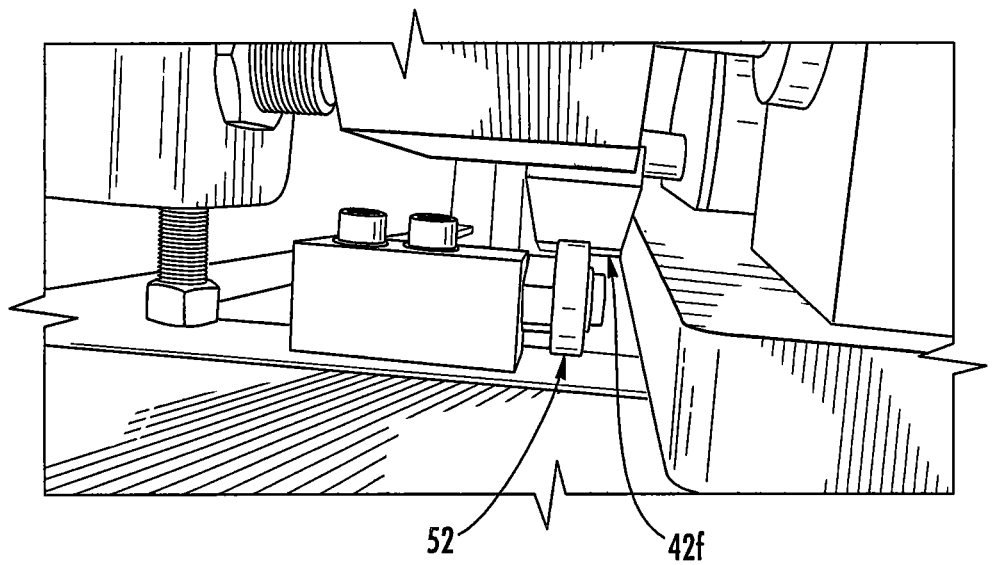

As the drive mechanism 100a continues to retract the load arm assembly 30a, the ramp 42 eventually engages the roller 52 as shown in FIG. 6D. Specifically, the sloped portion 42s of the ramp 42 first engages the roller 52. The drive mechanism 100a continues to retract the load arm assembly 30a until the flat portion 42f of the ramp sits on the roller 52 (FIG. 6F). At this point the load arm assembly 30a and the wheel 40 are in the rest position and the drive mechanism 100a no longer retracts the load arm assembly 30a.

Other configurations are contemplated to place the load arm assembly 30a and the wheel 40 in the rest position. As just one example, a protrusion may extend from the bottom portion 32b of the arm 32. The protrusion may be received in a recess (e.g., a ramped recess formed in the device housing 12). When the protrusion is received in the recess, a front portion of the arm 32 raises slightly, thereby raising the wheel 40.

Figure 11:
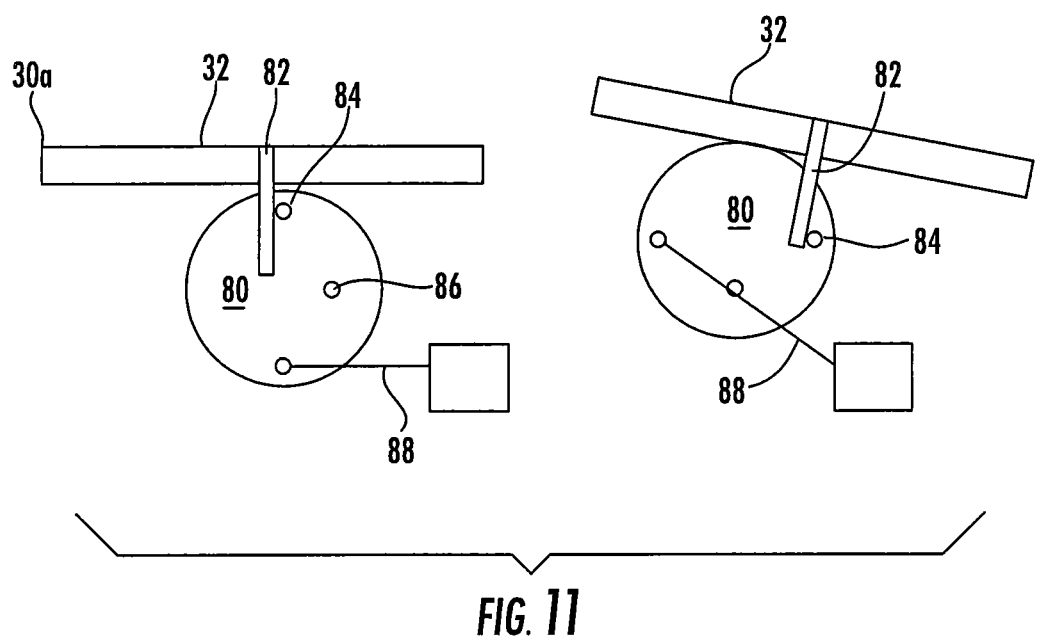
FIG. 11 is a schematic diagram illustrating an alternative load arm assembly that may be used with the device of FIG. 1.

Another possible configuration is illustrated in FIG. 11. This is an alternative embodiment using a cam 80. The load arm assembly 30a has a catch member 82. The catch member 82 engages cam pin 84 and as the load arm 32 is pulled back the cam 80 is forced to rotate around a cam point of rotation 86. Since the point of rotation 86 is offset the cam 80 forces the load arm 32 to raise. An elastic member 88 is employed and connected to the cam 80 so that the cam 80 returns to the original position when the load arm 32 moves forward.

The load arm assembly 30a is also shown retracted in the rest position in FIG. 2. In this position, the sample tray 18a holding the samples 20a can be removed from the tray holding unit 16a (e.g., after a test) and can be inserted into the tray holding unit 16a (e.g., before a test). Known wheel-tracking devices require a user to manually lift the weighted load arm and wheel or to connect a winch to a connection point on the load arm. These known devices are undesirable at least because the weighted load arm and wheel are heavy (e.g., to impart a wheel load of 705 N or 158 lbf during the AASHTO T324 test) and manually lifting the weighted load arm and wheel could lead to injury (and/or product liability). These known devices are also undesirable at least because of the extra equipment that may be required and the additional cost associated with inclusion of a lifting mechanism. In addition, samples are typically tested in a water bath of 50° C. (122° F.) and either manually lifting the load arm and wheel or connecting a winch thereto puts the user close to the water bath and at a burn risk.

In contrast, embodiments of the present invention provide an automated solution in which a user is not required to manipulate the heavy load arm assembly (30a, 30b) before inserting or removing a sample tray (18a, 18b).

Embodiments of the present invention use a weighted load arm assembly. The use of weight(s) provides a more consistent load on the samples than other devices that use pneumatic cylinders or the like to provide the load on the samples. These devices may not provide a consistent load on the samples during the rapid testing (for example, a feedback loop may not be adequate to account for real time changes in the test conditions).

Figure 7:
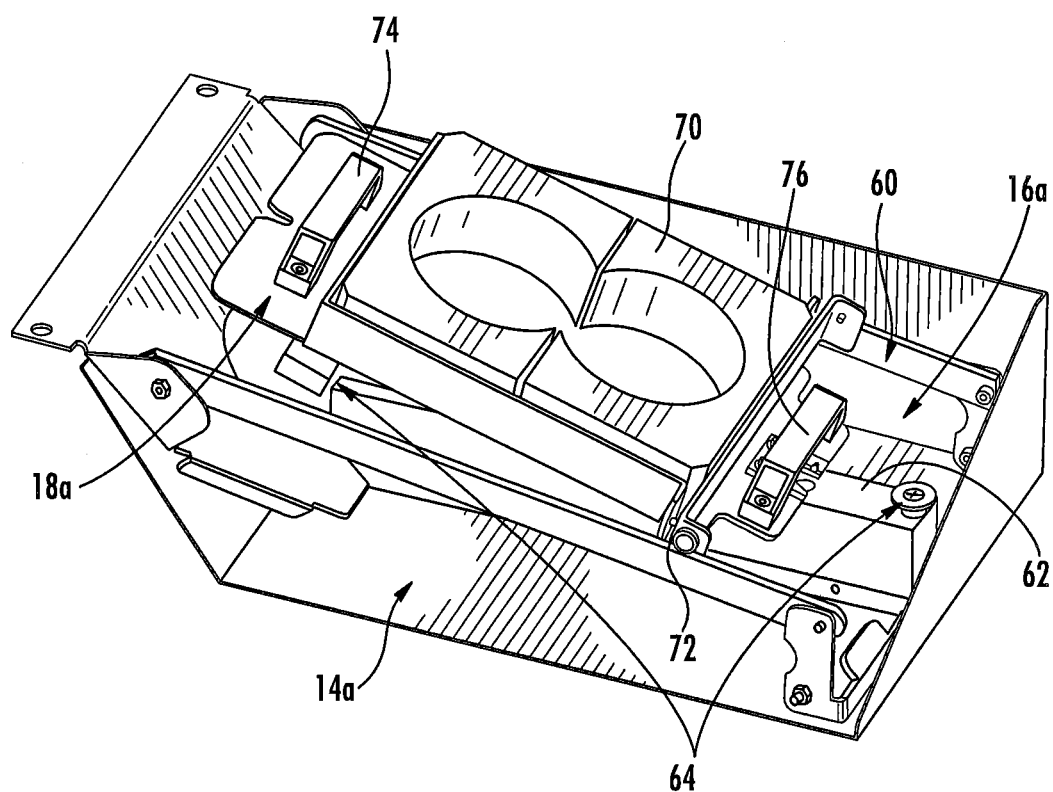
FIG. 7 is a perspective view of a tray holding unit and a sample tray used in the device of FIG. 1 according to some embodiments.

Further, the tray holding units 16a, 16b according to embodiments of the present invention facilitate easier and safer insertion and removal of the sample trays 18a, 18b. The sample chamber 14a is illustrated in FIG. 7. The sample chamber 14a may also be referred to as a "water bath" because the chamber is often filled or substantially filled with heated water during a wheel-tracking test (e.g., a test in compliance with AASHTO T324).

Still referring to FIG. 7, the tray holding unit 16a can include first and second spaced-apart rails or ramps 60 that are disposed on opposite sides of the chamber 14a. The rails 60 slope downwardly from a front portion 12f (FIG. 2) of the device housing 12 into the chamber 14a. The tray holding unit 16a also includes a tray support member 62 having a flat upper surface. The tray holding unit 16a further includes one or more tray locking mechanisms 64.

Although two rails 60 are shown in FIG. 7, it will be understood that a greater or lesser number of rails may be employed. For example, there may be one rail that is provided generally in the middle of the chamber 14a, with the rail sloping downwardly from the housing front portion 12f (FIG. 2) into the chamber 14a.

Still referring to FIG. 7, the sample tray 18a can include a sample holding member 70 on an upper surface of the tray 18a. The sample tray 18a also includes a pair of rotatable or slidable members 72 (only one is visible in FIG. 7). The members 72 are at a front portion of the tray 18a and are disposed on opposing sides of the tray 18a. The members 72 are positioned and configured to be received on the rails 60 of the tray holding unit 16a. The tray 18a can further include a handle 74 at a rear portion of the tray 18a and a handle 76 at the front portion of the tray 18a.

A user may load the tray 18a in the test chamber 14a as follows. The user grasps both handles 74, 76 and carries the tray 18a to the test chamber 14a. The user positions the front portion of the tray 18a such that the rotatable or slidable members 72 rest on the rails 60 of the tray holding unit 16a. The user may then grasp the handle 74 at the rear portion of the tray 18a to control the tray 18a as it slides down the rails 60 and into the test chamber 14a. As the tray 18a slides past the point shown in FIG. 7, the tray 18a comes to rest on the tray support member 62. The tray 18a (and test samples held in the sample holding member 72) is held in a generally horizontal position and the locking mechanism(s) 64 may secure the tray 18a at the front and/or rear portions thereof. This position is shown in FIG. 2.

The tray 18a and the specimens 20a held thereon (FIG. 2) typically weigh between about 35 and 50 pounds, so the mechanical assistance provided by the configuration of the tray holding unit 16a and the tray 18a reduces physical strain on the operator. Known wheel-tracking devices require the user to carefully align the tray with brackets or pins (e.g., align all four corners of the tray with brackets or pins and lower the tray onto the brackets). According to embodiments of the present invention, the tray 18a with specimens 20a can be inserted into the water bath 14a by rolling the tray 18a down the rails or ramps 60 instead of aligning the tray on small brackets or pins. The rails or ramps 60 allow the user to hold the tray 18a near waist-level and insert one end of the tray 18a into the water bath. The user can then use the handle 74 on the opposite end of the tray to lower the tray and the specimens into the bath. This removes the need for the user to lift the entire tray and lean over the water bath to insert the tray and therefore reduces the risk of injury such as back strain and burning from the hot water.

FIG. 8 illustrates further features of the device 10 according to some embodiments. The drive mechanisms 100a, 100b drive the load arm assemblies 30a, 30b, respectively. As noted above, the drive mechanisms are configured to advance the load arm assemblies to the load position, to reciprocate the load arm assemblies such that the wheels reciprocate over test specimens, and to retract the load arm assemblies to the rest position. Any suitable drive mechanism may be employed; in some embodiments, the drive mechanisms 100a, 100b include linear motors. The drive mechanisms 100a, 100b may be operated by at least one controller 102.

Each load arm assembly 30a, 30b can include or be in communication with a device for electronically measuring displacement such as a linear variable differential transducer (LVDT) device 104a, 104b. The LVDT device 104a is also shown in FIGS. 4A and 4B. The LVDT device 104a is configured to measure a depth of the impression of the wheel 40 during a test. The LVDT device 104a and the controller 102 are configured to determine rut depth during a test without stopping the wheel 40.

A water temperature control unit 106 can be configured to control the temperature of water in the test chambers 14a, 14b. The water temperature control unit 106 and/or the controller 102 may maintain a substantially constant and elevated water temperature in the test chambers 14a, 14b during a test procedure.

Figure 9A:
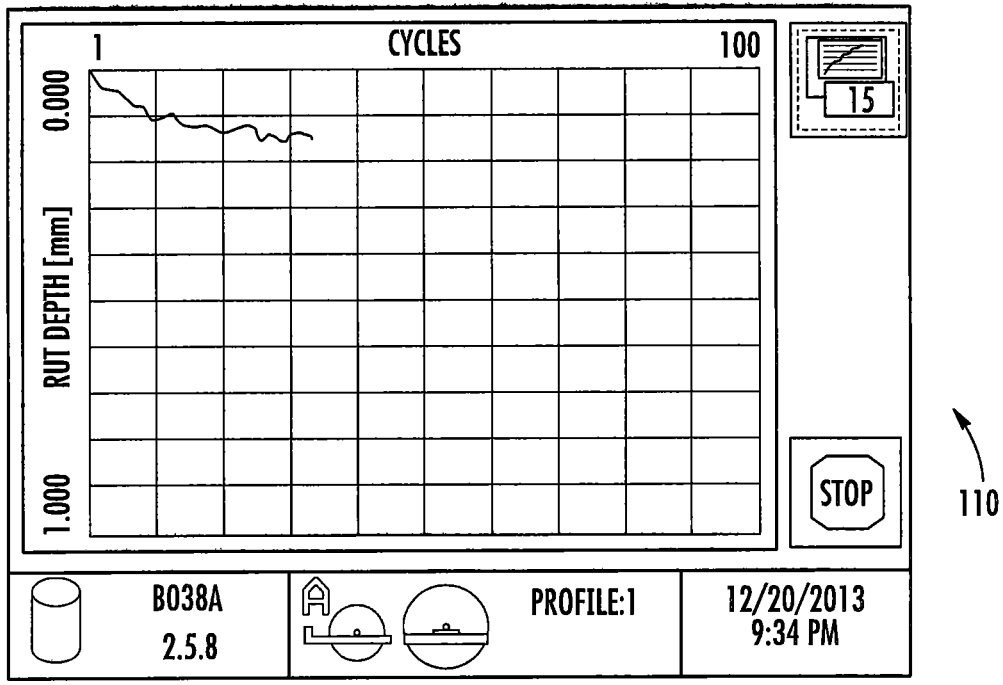
FIGS. 9A and 9B are exemplary screenshots of a display of the device of FIG. 1 according to some embodiments.
Figure 9B:
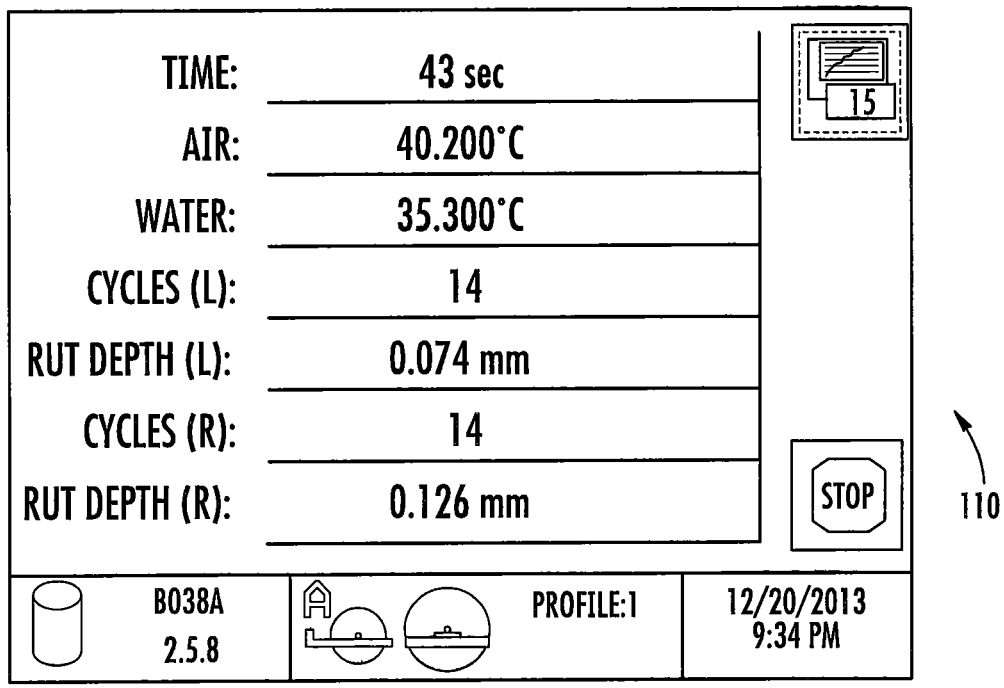

The device 10 may include a display 110 and/or a user interface 112 (which may be integrated with the display 110 as a touch sensitive display). The user interface 112 can allow a user to input test parameters before a test and make adjustments during a test (e.g., stop the test). FIGS. 9A and 9B are exemplary screenshots of the display 110 during a test. Rut depth is automatically calculated and shown graphically in real time in the screenshot of FIG. 9A and tabularly in FIG. 9B along with other operating parameters.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention. Therefore, it is to be understood that the foregoing is illustrative of the present invention and is not to be construed as limited to the specific embodiments disclosed, and that modifications to the disclosed embodiments, as well as other embodiments, are intended to be included within the scope of the invention.

That which is claimed is:

1. A wheel-tracking test device comprising:
a housing;
one or more test chambers in the housing, each test chamber configured to receive and hold one or more asphalt test samples;
one or more load arm assemblies, each load arm assembly comprising:
a weighted loading arm; and
a wheel rotatably connected to the loading arm; and
a drive mechanism configured to move the load arm assembly from a load position in which the wheel is on a test sample held in the test chamber to a rest position by retracting the loading arm such that the wheel is lifted off the test sample,
wherein:
the housing has a ramp engagement member;
each load arm assembly has a ramp on a bottom portion of the loading arm; and
the drive mechanism is configured to move the load arm assembly from the load position to the rest position by retracting the loading arm such that the ramp engages the ramp engagement member and the wheel is lifted off the test sample.

2. The device of claim 1, wherein, when the load arm assembly is in the load position, the drive mechanism is configured to move the wheel to reciprocate over the one or more test samples.

3. The device of claim 1, wherein each test chamber includes a tray receiving unit that is configured to receive and hold a sample tray that holds the one or more test samples.

4. The device of claim 1, wherein the device is a test device in compliance with AASHTO T324.

5. The device of claim 1, wherein, in the rest position, a flat portion of the ramp sits on the ramp engagement member.

6. The device of claim 1, further comprising an actuator that resides above the loading arm and vertically translates to pivot an end portion of the arm and raise/lower the wheel.

7. The device of claim 1, wherein the weighted loading arm includes at least one weight at a distal end portion of the arm.

8. The device of claim 7, wherein the weighted loading arm has a weight that applies a wheel load of about 705 N or 158 lbf on the test sample in the load position.

9. The device of claim 1, wherein, when the load arm assembly is in the load position, the drive mechanism is configured to move the wheel to reciprocate over the one or more test samples such that the position of the wheel varies sinusoidally over time.

10. A wheel-tracking test device comprising:
a housing;
one or more test chambers in the housing, each test chamber configured to receive and hold one or more asphalt test samples;
one or more load arm assemblies, each load arm assembly comprising:
a weighted loading arm; and
a wheel rotatably connected to the loading arm; and
a drive mechanism configured to move the load arm assembly from a load position in which the wheel is on a test sample held in the test chamber to a rest position by retracting the loading arm such that the wheel is lifted off the test sample,
wherein each test chamber includes a tray receiving unit that is configured to receive and hold a sample tray that holds the one or more test samples,
wherein the tray receiving unit includes one or more rails that slope downwardly from a front portion of the housing, each rail configured to receive a front portion of a sample tray such that the sample tray is slidable down the one or more rails and into the test chamber.

11. The device of claim 10, wherein the tray receiving unit includes a tray holding member, the tray holding member having a flat upper portion configured to hold the sample tray and the one or more test samples in a horizontal position.

12. The device of claim 11, wherein the tray receiving unit includes one or more locking mechanisms configured to hold the sample tray in place in the horizontal position.

13. The device of claim 12 in combination with a sample tray holding one or more hot mix asphalt samples, the sample tray comprising:
a tray body;
a sample holding member on a top surface of the tray body with the one or more samples held in the sample holding member;
one sliding mechanism on each opposite side of the tray body at a front portion of the tray body;
a first handle at the front portion of the tray body; and
a second handle at a rear portion of the tray body.

14. The device of claim 10, wherein:
the housing has a ramp engagement member;
each load arm assembly has a ramp on a bottom portion of the loading arm; and
the drive mechanism is configured to move the load arm assembly from the load position to the rest position by retracting the loading arm such that the ramp engages the ramp engagement member and the wheel is lifted off the test sample.

15. A method of performing an asphalt sample test, the method comprising:
slidably inserting a sample tray holding one or more asphalt samples into a test chamber;
automatically advancing a weighted load arm assembly to a load position using a drive mechanism, wherein in the load position a wheel of the load arm assembly is on the one or more asphalt samples;
automatically reciprocating the wheel over the one or more asphalt samples using the drive mechanism to perform a wheel-track test;
automatically retracting the load arm assembly to a rest position using the drive mechanism, wherein in the rest position the wheel is off the one or more asphalt samples, and wherein the retracting step is carried out to retract the load arm assembly such that a ramp on a bottom portion of the load arm assembly engages a ramp engagement member and the wheel is lifted off the one or more asphalt samples; and slidably removing the sample tray from the test chamber.

16. The method of claim 15, wherein the retracting step is carried out to retract and pivot the load arm assembly to raise the wheel off the one or more asphalt samples before the slidably removing step.

17. The method of claim 15, wherein the reciprocating step is carried out to perform a wheel-track test in compliance with AASHTO T324.

18. A method of performing an asphalt sample test, the method comprising:

providing a test device comprising a housing and a test chamber in the housing, wherein one or more rails slope downwardly from a front of the housing into the test chamber;

slidably inserting a sample tray holding one or more asphalt samples into the test chamber by receiving a front portion of the sample tray on the one or more rails and sliding the sample tray down the one or more rails into the test chamber;

automatically advancing a weighted load arm assembly to a load position using a drive mechanism, wherein in the load position a wheel of the load arm assembly is on the one or more asphalt samples;

automatically reciprocating the wheel over the one or more asphalt samples using the drive mechanism to perform a wheel-track test; and automatically retracting the load arm assembly to a rest position using the drive mechanism, wherein in the rest position the wheel is off the one or more asphalt samples.

19. The method of claim 18, further comprising slidably removing the sample tray from the test chamber after the retracting step.

20. The method of claim 19, wherein the slidably removing step is carried out by grasping a handle on a rear portion of the sample tray and sliding the sample tray up the one or more rails out of the test chamber.

* * * * *